United States Patent
Gallagher et al.

(12)

(10) Patent No.: US 6,589,757 B1
(45) Date of Patent: Jul. 8, 2003

(54) SEQUENCE ANALYSIS OF SACCHARIDE MATERIAL

(75) Inventors: John Thomas Gallagher, Cheshire (GB); Jeremy Ewan Turnbull, Kidderminster (GB); John Joseph Hopwood, Stonyfell (AU)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 08/836,399

(22) PCT Filed: Oct. 30, 1995

(86) PCT No.: PCT/GB95/02541

§ 371 (c)(1),
(2), (4) Date: Oct. 20, 1997

(87) PCT Pub. No.: WO96/13606

PCT Pub. Date: May 9, 1996

(30) Foreign Application Priority Data

Oct. 29, 1994 (GB) ............................................. 9421819

(51) Int. Cl.[7] .................................................. C12Q 1/54
(52) U.S. Cl. ........................................ 435/14; 536/124
(58) Field of Search .................... 435/14, 18; 536/1.11, 536/4.1, 17.2, 124

(56) References Cited

FOREIGN PATENT DOCUMENTS

| EP | 421 972 | 4/1991 |
|---|---|---|
| EP | 0 421 972 A2 | * 10/1991 |
| WO | 92/02816 | 11/1992 |
| WO | 92/19768 | 11/1992 |
| WO | 92/19974 | 11/1992 |
| WO | WO 92/19974 | * 11/1992 |

OTHER PUBLICATIONS

Kyung–Bok L., A New Method for Sequencing Linear Ologosaccharides on Gels Using Charged, Fluorescent Conjugates, Carbohydrate Research 214(1)155–168. Jul. 1991.*

Mizuochi T., Microscale Sequencing of N–Linked Oligosaccharides of Glycoproteins Using Hydrazinolysis, Bio–Gel P–4, and Sequential Exoglycosidase Digestion, Methods in Molecular Biology vol. 14 55–68. 1993.*

Cancilla M, Alkaline Degradation of Oligosaccharides Coupled with Matrix–Assisted Laser Desorption/Ionization Fourier Transform Mass Spectrometry: A Method for Sequencing Oligosaccharides, Anal Chem 70(14)663–672. Feb. 1998.*

Carbohydrate Research, vol. 214, No. 1, Jul. 18, 1991, pp. 155–168, XP 000226749, Kyung–Bok Lee et al: A New Method for Sequencing Linear Oligosaccharides on Gels Using Charged, Fluorescent Conjugates, see p. 155, see p. 163.

The Journal of Biological Chemistry,, vol. 269, No. 35, Sep. 2, 1994. pp. 22391–22396, N.Parthasarathy et al: "Oligosaccharide sequences of endothelial cell surface heparan sulfate proteoglycan with a affity for lipoprotein lipase.".

Biochemistry, vol. 15, No. 18, 1976, pp. 3932–3942, J. E.Shively et al: "Formation of anhydrosugars in the chemical depolymerization of heparin.".

* cited by examiner

Primary Examiner—Ralph Gitomer
(74) Attorney, Agent, or Firm—Pillsbury Winthrop LLP

(57) ABSTRACT

A method of analyzing and sequencing saccharide material composed of saccharide chains. The saccharide chains are end referenced, e.g., by labeling or tagging at their reducing ends, and the saccharide material is subjected to a controlled partial depolymerisation using a selection scission reagent, for example, low pH nitrous acid, which cleaves internal glycosidic linkages in accordance with known linkage specificity so as to produce a mixed set of saccharide chain fragments having different lengths ranging throughout the full spectrum of possible lengths for the particular glycosidic linkage specificity of the selective scission reagent employed. Samples of the mixed set of saccharide chain fragments are then treated with selected exoenzymes including exoglycosidases that cleave only particular glycosidic linkages at the non-reducing end of saccharide chains. These exoenzymes are applied to the samples either singly or in combination in accordance with a predetermined strategy. The treated samples are then analyzed, to detect the chain fragments present which have a reducing end derived from the reducing end of the corresponding chain in the original saccharide material and the monosaccharide sequence in the saccharide starting material is then deduced.

18 Claims, 3 Drawing Sheets

US 6,589,757 B1

SEQUENCE ANALYSIS OF SACCHARIDE MATERIAL

FIELD OF THE INVENTION

The present invention is concerned with sequence analysis of saccharide material and it is especially applicable to the sequencing of saccharide chains containing numerous amino sugar residues such as, for example, are found in glycosaminoglycans (GAG's) which include the biologically important polysaccharides, heparan sulphate (HS) and heparin.

BACKGROUND

Heparan sulphate (HS) and heparin are chemically-related linear glycosaminoglycans (GAG's) composed of alternate α,β-linked glucosamine and hexuronate residues with considerable structural variation arising from substitution with acetyl and N- and O-sulphate groups, and from the presence of D- and L-isomers of the hexuronate moieties. These polysaccharides are of fundamental importance for many diverse cellular and biochemical activities. Their regulatory properties are dependent on their ability to bind, and in some cases to activate, protein molecules which control cell growth, cell adhesion, and enzyme-mediated processes such as haemostasis and lipid metabolism. However, analysis of protein-binding monosaccharide sequences in HS/heparin is generally difficult and a universal procedure suitable for routine use has not been described to date.

An object of the present invention is to provide a new method of sequence analysis of saccharide fragments such as oligosaccharides that may be derived from HS (or heparan sulphate proteoglycan HSPG) and heparin, this method enabling rapid elucidation of recognition sites and other sequences of interest and thereby facilitating the rational design of synthetic compounds to serve as drugs for therapeutic modulation of polysaccharide function.

SUMMARY OF THE INVENTION

In one aspect the invention may be regarded as being based on a concept of bringing about a preliminary partial depolymerisation by scission of specific intrachain linkages in reducing end referenced saccharide chains, such as for example HS/heparin saccharide chains, followed by exoenzyme removal of non-reducing end (NRE) sugars or their sulphate groups so as to yield a range of labelled fragments that can be separated by gel electrophoresis or other appropriate techniques to give a read-out of the sequence of sugar units and their substituents. Although the invention may be described mainly in relation to saccharides that are found in heparan sulphate and heparin, the basic principle of the sequencing strategy is applicable to many other GAG's and different saccharides, including the saccharide component of glycoproteins.

Use of exoenzymes, in particular exoglycosidsases, for removal of terminal sugar residues at the non-reducing end of saccharide chains has previously been proposed in connection with methods for sequencing such chains, for instance in WO 92/02816 and in WO 92/19974 and WO 92/19768. However, in these prior art proposals there has been no preliminary step of partial depolymerisation of the saccharide material, involving cleavage of internal glycosidic linkages, before treatment with said exoenzymes. In WO 92/02816 for example, it is proposed in relation to a saccharide sequencing method disclosed therein to use exoenzymes successively to remove and identify terminal sugar residues at the non-reducing end of initially undegraded saccharide chains, and to carry out a series of sequential steps with the residual saccharide material being recovered after each step before proceeding to the next. In WO 92/19974 and WO 92/19768, although exoenzymes are mentioned inter alia as possible sequencing agents, again it is proposed that these be applied sequentially direct to an oligosaccharide being analysed in an iterative process without a preliminary partial depolymerisation step as required by the present invention. In all these prior art methods the sequencing information is obtained and presented in a different manner to that in the present invention.

An acknowledgement is also made of a paper by Kyung-Bok Lee et al, Carbohydrate Research, 214 (1991), 155–168, which refers to the use of exoglycosidases and of endoglycosidases in connection with sequencing of oligosaccharides. This publication does not, however, disclose the combined use of both exoglycosidases and endoglycosidases in sequence in the same manner as herein defined in the claims relating to the present invention.

More specifically, the present invention broadly provides a method of analysing and sequencing saccharide material comprising saccharide chains which contain more than three monosaccharide units interconnected through glycosidic linkages that are not all identical and which each include a referencing feature at their reducing end, wherein selected exoenzymes comprising exoglycosidases of known specificity that cleave only particular glycosidic linkages at the non-reducing end of saccharide chains are used to obtain sequence information, said method being characterised in that it comprises the sequential steps of:

(a) subjecting said saccharide material to partial depolymerisation by controlled treatment with a selective scission reagent that acts in accordance with a known predetermined linkage specificity as an endoglycosidase to cleave a proportion of susceptible internal glycosidic linkages, that is, susceptible glycosidic linkages spaced from the non-reducing end of the saccharide chains, thereby to produce a mixed set of saccharide chains, intact chains and fragments of intact chains, having different lengths representative of the full spectrum of all possible lengths given the particular glycosidic linkage specificity of the selective scission reagent employed, (b) treating a selected sample or samples of said mixed set of saccharide chains and chain fragments with said exoenzymes, either singly or in combination in accordance with a predetermined strategy, to an extent sufficient to obtain complete digestion and cleave susceptible linkages at the non-reducing end of all the saccharide chains, and then (c) analysing said sample or samples to detect the various saccharide chain fragments generated by the cleavage treatments which are present therein and which have a reducing end derived from the reducing end of the corresponding chain in the original saccharide material, and obtaining, collectively from the results of said analysis, information enabling the monosaccharide sequence in the original saccharide material to be at least partially deduced.

In carrying out this saccharide sequencing method of the present invention, the saccharide material will generally be treated, usually before the controlled partial depolymerisation step, to modify the saccharide chains at their reducing ends in order to introduce the reducing end referencing feature for providing a common reference point or reading frame to which the monosaccharide sequence can be related and for facilitating, during analysis, detection of chain fragments having a reducing end derived from the reducing end of the corresponding chains in the original saccharide material. This end referencing feature is conveniently provided by selectively labelling or tagging the monosaccharide units at the reducing ends of the saccharide chains, using for example radiochemical, fluorescent, biotin or other calorimetrically detectable labelling means.

If low pH nitrous acid is used for carrying out the partial depolymerisation of the saccharide material as hereinafter described, a presently preferred fluorescent labelling agent is anthranilic acid as referred to in more detail later. However, if a selective scission reagent other than nitrous acid is used for bringing about the partial depolymerisation, e.g. an endoglycosidase enzyme, an aminocoumarin hydrazide, e.g. 7-amino4-methylcoumarin-3-acetyl hydrazide, may be preferred for providing a fluorescent labelling agent having a relatively high labelling efficiency. For use as a radiochemical labelling agent tritiated borohydride may be used.

In an alternative but usually less preferred technique for providing end-referenced saccharide chains or chain fragments, the chains may be immobilized by coupling the reducing ends to a solid phase support. This can then permit those chain fragments, produced by the partial depolymerisation treatment, which are not contiguous with the reducing ends of the original undegraded chains to be physically separated and removed, whereupon subsequent release of the immobilized chain fragments from the solid phase support then provides the required mixed set of chain fragments ready for exoenzyme treatment as before.

In preferred embodiments, as hereinafter more fully described, electrophoretic separation means such as polyacryiamide gel electrophoresis (PAGE), e.g. gradient PAGE, will usually be used for detecting the fragments produced by the cleavage treatments, these fragments being separated according to differences in length and composition which are reflected in different mobilities in the electrophoretic medium. If necessary, for uncharged or lightly charged saccharide chains, the material can be treated in a preliminary operation so as to incorporate therein suitable electrically charged groups in a known manner in order to permit the use of electrophoretic separation techniques. This will not usually be necessary, however, in sequencing HS or heparin oligosaccharides which already contain a significant number of charged sulphate and carboxyl groups. Other alternative separation techniques, for example capillary electrophoresis or high performance liquid chromatography (HPLC), may also be used for detecting the fragments so long as the requisite resolving power is available.

After the controlled partial depolymerisation step the mixed set of saccharide chain fragments produced will usually be used to provide a number of separate samples. One of these samples, and generally a control sample of the original material, will then be subjected to the separation technique, e.g. gradient PAGE, to separate and detect the different fragments present for reference purposes before exoenzyme treatment. At the same time, other samples of the set of fragments will also be subjected to the same separation technique so as to separate and detect the different saccharide fragments present after each of these other samples has been treated with a different exoenzyme or combination of exoenzymes.

In applying the invention to the sequencing of saccharide chains containing many amino sugar residues, such as are found in glycosaminoglycans (GAG's) for which the method is especially useful, the preliminary controlled partial depolymerisation involving cleavage of specific internal glycosidic linkages is most conveniently carried out as hereinafter more fully described using nitrous acid at low pH as a chemical selective scission reagent. It is also possible, however, in some cases as an alternative to a chemical selective scission agent to use appropriate enzymatic endoglycosidases, e.g. the bacterial lyases heparinase (EC 4.2.2.7) or heparitinase (EC 4.2.2.8), under suitable conditions to bring about selective enzymatic cleavage of internal glycosidic linkages.

As GAG's and similar saccharides also generally contain various sulphated monosaccharide units, the selected exoenzymes used for treating tile fragments obtained after the initial hydrolysis and partial depolymerisation will usually include, in addition to exoglycosidases, selected exosulphatases for effecting a controlled removal of particular sulphated groups from specific terminal monosaccharide residues at the non-reducing end of the chains. Other additional specific enzymes may also be used in analysing the fragments obtained after the partial depolymerisation as part of the overall strategy selected for extracting or confirming the sequence information required.

Examples of selective scission reagents which may be used in carrying out the sequencing method of the present invention include the following:

| | Reagents | Linkage Specificity |
|---|---|---|
| (1) | *Nitrous Acid | $GlcNSO_3 \rightarrow HexA$ |
| (2) | *Glucuronidase (Gase) (β-D-glucuronidase) | $GlcA \rightarrow GlcN.R$ |
| (3) | *Iduronidase (Idase) (α-L-iduronidase) | $IdoA \rightarrow GlcN.R$ |
| (4) | *N-acetylglucosaminidase | $GlcNAc \rightarrow HexA$ |
| (5) | ■Iduronate-2-Sulphatase (I2Sase) | IdoA ⎯⎯→ GlcN.R<br>\|<br>[2s] |
| (6) | ■Glucosamine-6-Sulphatase (G6Sase) | GlcN.R ⎯⎯→ HexA<br>\|<br>[6s] |
| e.g. | ■N-acetylglucosamine-6-sulphatase | GlcNAc ⎯⎯→ IdoA<br>\|<br>[6s] |
| (7) | *Glucuronate-2-Sulphatase | GlcA ⎯⎯→ GlcN.R<br>\|<br>[2s] |
| (8) | ■Sulphamate sulphohydrolase | $GlcNSO_3 \rightarrow HexA$ |

Abbreviations and labels used above have the following meanings:
GlcN. = Glucosamine
R = Acetyl (Ac) or $SO_3$-
HexA = Hexuronic acid
GlcA = Glucuronate
IdoA = Iduronate
*Cleaves glycosidic linkages
■Removes sulphate groups only The enzymes mentioned above are exoenzymes which act specifically to remove the terminal sugar residues or their sulphate substituents at the non-reducing end (NRE) of glycan fragments. Details of many such enzymes are readily available in the literature, and by way of example reference may be had to an informative review article entitled "Enzymes that degrade heparin and heparan sulphate" by John J. Hopwood in "Heparin: Chemical and Biological Properties, Clinical Applications", pages 191 to 227, edited by D. A. Lane et al and published by Edward Arnold, London, 1989, and to another review article entitled "Lysosomal Degradation of Heparin and Heparan Sulphate" by Craig Freeman and John Hopwood in "Heparin and Related Polysaccharides", pages 121 to 134, also edited by D. A. Lane et al and published by Plenum Press, New York, 1992.

Some of these enzymes are available commercially and others can be isolated and purified from natural sources as described in the literature. Moreover, in some cases recombinant versions are known and, when available, these will often be preferred because of a high level of purity that can usually be achieved. Published papers in which the isolation and preparation or properties of some of the enzymes referred to above are described include: Alfred Linker, (1979), "Structure of Heparan Sulphate Oligosaccharides and their Degradation by Exo-enzymes", *Biochem. J.*, 183, 711–720; Craig Freeman and John J Hopwood, (1992), "Human α-L-iduronidase", *Biochem. J.*, 282, 899–908; Wolfgant Rohrborn and Kurt Von Figura, (1978), "Human Placenta α-N-Acetylglucosaminidase: Purification. Characterisation and Demonstration of Multiple Recognition Forms", *Hoppe-Seyler's Z. Physiol. Chem.*, 359, 1353–1362; Craig Freeman and John J Hopwood, (1986), "Human Liver Sulphamate sulphohydrolase", *Biochem. J.*, 234, 83–92: Craig Freeman, et al, (1987), "Human Liver N-acetylglucosamine-6-sulphate sulphatase", *Biochem. J.*, 246, 347–354; Craig Freeman and John J Hopwood, (1991), "Glucuronate-2-sulphatase activity in cultured human skin fibroblast homogenates". *Biochem. J,.* 279. 399–405: Craig Freeman and John J Hopwood, (1987), "Human liver N-acetylglucosamine-6-sulphate sulphatase", *Biochem. J.*, 246. 355–365: Irwin G. Leder (1980), "A novel 3-O sulfatase from human urine acting on methyl-2-deoxy-2-sulfamino-α-D-glucopyranoside 3-sulphate", *Biochemical and Biophysical Research Communications*, 94, 1183–1189; Julie Bielicki, et al, (1990), "Human liver iduronate-2-sulphatase", *Biochem. J.*, 271. 75–86: Irwin G. Leder (1980), "A novel 3-O sulfatase from human urine acting on methyl-2-deoxy-2-sulfamino-α-D-glucopyranoside 3-sulphate", *Biochemical and Biophysical Research Communications*, 94, 1183–1189; and Julie Bielicki, et al, (1980), "Evidence for a 3-O-sulfated D-glucosamine residue in the antithrombin-binding sequence of heparin", *Biochemistry*, 77, 6551–6555.

A recombinant version of an exoenzyme and the preparation thereof is described for example in connection with a synthetic α-L-iduronidase in international patent publication WO 93/10244.

The contents of the above-mentioned publications are incorporated herein by reference.

The nitrous acid ($HNO_2$) reagent used at low pH cleaves hexosaminidic linkages when the amino sugar is N-sulphated ($GlcNSO_3$) irrespective of the position of the linkage in the saccharide chain, but most importantly GlcNAc→GlcA linkages are resistant to $HNO^2$ scission. The controlled hydrolysis and partial depolymerisation with nitrous acid can be achieved by preparing the reagent as described by Steven Radoff and Isidore Danisliefsky,*J. Biol. Chem.* (1984), 259, pages 166–172 a publication of which the content is also incorporated herein by reference. A typical example with practical details, however, is described below.

Example of Conditions for Nitrous Acid Hydrolysis and Partial Depolymerisation of Saccharides The saccharide to be treated (1–2 nmoles) is dried down by centrifugal evaporation, dissolved in 80 μL of distilled $H^2O$ and cooled on ice. To this solution is added 10 μL of 190 mM HCl and 10 μL of 10 mM $NaNO_2$, both precooled on ice. These reactants are mixed by vortexing and incubated on ice. At predetermined time points (for example 0, 20, 40, 60, 90 and 120 minutes), aliquots of the reaction mixture are removed and the low pH $HNO_2$ hydrolysis is stopped either by addition of excess ammonium sulphamate to quench the reagent, or by raising the pH above 4.0 (for example by addition of $Na_2CO_3$ solution). It has in fact been found most convenient to stop the reaction by addition of 1/4 volume of 200 mM sodium acetate buffer, pH 5.0. This raises the pH to approximately pH 4.3–4.4 and provides buffer conditions immediately compatible with subsequent enzyme treatments, thus avoiding the need for any further clean-up steps such as removal of salts or buffer exchanges. Finally, once all the time points are complete the aliquots are remixed and pooled. This is crucial since it creates a mixed set of saccharide products, hydrolysed partially and at random, which contain fragments corresponding to all possible cleavage positions, whereas a single time point would not create such a representative set. Thus, the fragments have different lengths ranging throughout the full spectrum of possible lengths for the particular glycosidic linkage specificity of the $HNO_2$ reagent, and ideally there should be a fairly even distribution of the different length fragments.

In carrying out the invention, it will be appreciated that in effect the controlled, incomplete hydrolysis of N-sulphated disaccharides by the $HNO_2$ treatment, i.e. the partial $HNO_2$ scission or depolymerisation (herein denoted as $pHNO_2$), is used to "open-up" the glycan structure of the saccharide material under analysis so as to expose a range of NRE sugars and sulphate groups to attack by specific exoglycosidases and exosulphatases. Indeed, this dual approach of combining a preliminary controlled hydrolysis and partial depolymerisation involving cleavage of internal linkages with a progressive action of exoenzymes acting at the non-reducing end of the fragments produced can be regarded as being an important and significant key feature characterising the sequencing method of this invention.

MORE DETAILED DESCRIPTION

The invention and the manner in which it may be carried out will now be hereinafter described in more detail with reference to non-limiting illustrative examples.

BRIEF DESCRIPTION OF THE DRAWINGS

In connection with the above-mentioned illustrative examples, reference should be made to the accompanying drawings in which.

EXAMPLE 1

Figure 1A:
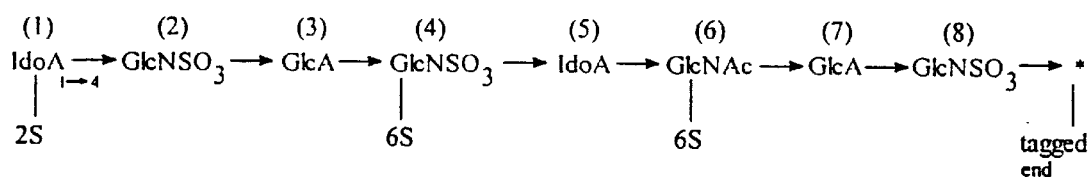
FIG. 1A represents a hypothetical but possible structure of an octasaccharide (degree of polymerisation dp=8) fragment that may be derived from heparan sulphate (HS) or heparin.

For sequencing the octasaccharide fragment illustrated in FIG. 1A of the accompanying drawings, initially the GlcNSO$^3$— unit at the reducing end (unit 8) is labelled or "tagged" using any one of a number of well-known techniques to introduce, for example, a radiochemical, fluorescent or biotin label which will enable specific detection of saccharides containing the tag and, most importantly, which will provide a reference point or reading frame at the reducing end (RE) from which the sequence can be read along the saccharide chain.

Use of a fluorescent compound to provide the label or tag will often be a preferred option, but when partial depolymerisation of the saccharide chain is subsequently to be carried out by low pH nitrous acid, as in the present example, it is important to select a fluorescent compound whose fluorescence is not likely to be quenched by the nitrous acid. Thus, although it has been found that high coupling efficiencies can be achieved using an aminocoumarin hydrazide reagent (e.g. 7-amino4-methylcoumarin-3-acetyl hydrazide, available from Pierce Ltd. U.K.) as a fluorescent label or tag, unfortunately it has been found that this is unsatisfactory for this present example because the fluorescence is quenched by nitrous acid. This labelling reagent, however, should be quite satisfactory for use when alternative selective scission reagents are employed to carry out the partial depolymerisation.

In the present case, therefore, the preferred fluorescent tag to use is anthranilic acid (2-aminobenzoic acid: ABA: excitation maxima, 290 nm, emission maxima, 390 nm) which is convenient and reasonably efficient. This reagent can be coupled specifically to the reducing end of sugars by reductive animation as described previously by K. R. Anumula (1994) *Analytical Biochemistry*, 220, 275–283, but with some modifications as described below.

For sulphated saccharides from GAGs at least, the following reaction conditions have been found to be satisfactory. The saccharides to be coupled (20–100 nmoles) are dried down in a microcentrifuge tube by centrifugal evaporation, dissolved directly in 250 µL of formamide containing 200 mM ABA and 100 mM reductant (sodium cyanoborohydride), and heated at 50° C. for 16–24 hours.

After coupling free ABA, reductant and formamide can conveniently be removed from tagged saccharides by methods such as dialysis, weak anion exchange chromatography or gel filtration chromatography. The latter is generally preferred since it usually allows quantitative recoveries of loaded sample. The following procedure has been found to be convenient. The sample (250 µL of reaction mixture diluted to a total of 1 mL with distilled water) is loaded onto two 5 mL HiTrap™ Desalting columns (products of Pharmacia Ltd). These are connected in series and eluted with distilled water at a flow rate of 1 mL/min. Fractions of 0.5 mL are collected. Saccharides consisting of 4 or more monosaccharide units typically elute in the void volume (approximately fractions 7–12). These fractions are pooled and concentrated by freeze drying or centrifugal evaporation. This approach allows rapid purification of tagged saccharide material from free tagging reagent, gives quantitative recoveries and the product is free of salts which might interfere with subsequent enzymic conditions.

It has been observed that die fluorescence spectra of saccharide-ABA conjugates is modified as compared to that of the free ABA. Typically the conjugates display an excitation maxima in the range 300–320 nm, which is ideal for visualistion with commonly available 312 nm UV sources (e.g. lamp or transilluminator). Emission maxima are typically in the range 400–420 nm (bright violet fluorescence).

Following coupling with fluorescent tags the saccharides can be further purified if required prior to sequencing using techniques such as anion exchange HPLC or gradient PAGE. The latter has been found to be particularly useful for purification purposes since it allows excellent resolution of tagged saccharides which can be readily recovered by electrotransfer to positively charged nylon membrane as described for example by Turnbull sand Gallagher in *Biochemical Journal* (1988) 251. 597–608 and, with additional modifications, in *Biochemical Journal* (1991) 265. 715–724. Again, the content of these publications is incorporated herein by reference. In this technique the appropriate bands in the electrophoresis gel are cut out, their position being established using a UV lamp (254 or 312 nm wavelength). The saccharides can be dissociated from the membrane by incubation in 5M sodium chloride solution in a microcentrifuge tube on a rotating mixer at 37° C. for 5 hours, and can then be desalted by chromatography of the solution on HiTrap™ Desalting columns as described above. This approach is particularly useful for preparing saccharides for sequencing from samples which are not purified to homogeneity prior to the fluorescent tagging step. Indeed, since gradient PAGE resolves many saccharides more effectively than other methods (for example anion exchange HPLC), it is the method of choice for preparing homogeneous saccharide species for sequencing.

Figure 1B:
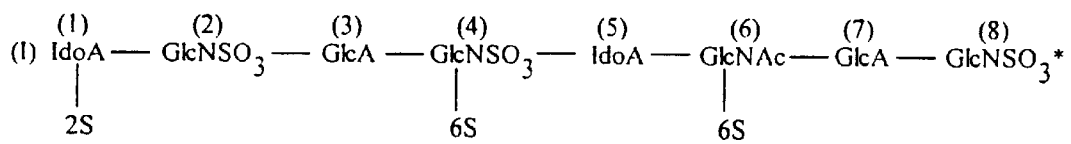
FIG. 1B shows the octasaccharide of FIG. 1A after partial depolymerisation which provides a mixed set of saccharide chain fragments.
Figure 1B:
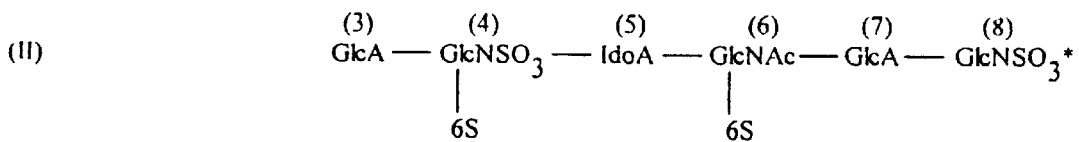
Figure 1B:
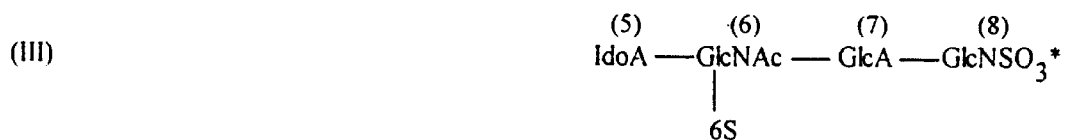

Upon treating the dp8 fragment illustrated in FIG. 1A with pHNO$_2$ as hereinbefore described a mixture of end-labelled or tagged fragments (herein referred to as pHNO$_2$ fragments) each with newly exposed NRE will be produced, as illustrated in FIG. 1B of the accompanying drawings.

Figure 2:
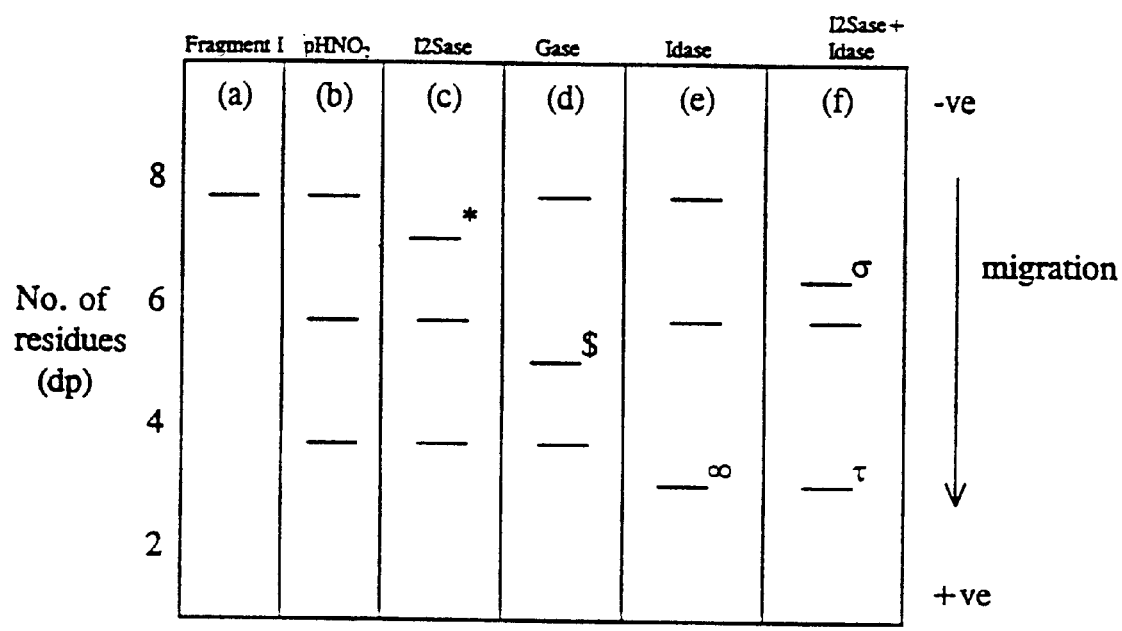
FIG. 2 is a chart or diagram illustrating the electrophoretic separation and analysis using PAGE of the set of saccharide chain fragments shown in FIG. 1B following exoenzyme treatment in accordance with the invention.

In the next stage, samples, preferably aliquots, of the mixture containing the pHNO$_2$ fragments are treated separately with different specific enzymes (singly or in combination) to remove accessible sulphate groups and sugar residues, and the resulting saccharides are then separated by gradient polyacryiamide gel electrophoresis (gradient PAGE) carried out in respect of each portion. This results in a banding pattern that may be visualized as indicated in the diagram of FIG. 2 in the accompanying drawings.

For simplicity this particular example describes only the use of enzymes to remove the terminal sulphated and non-sulphated hexuronates, but in practice a small number of additional treatments may be needed to achieve a complete sequence identification. Samples of the pHNO$_2$ fragments are treated separately with iduronate-2-sulphatase, glucuronidase and iduronidase and with the combination of iduronate-2-sulphatase plus iduronidase. These enzyme treated samples are each analysed separately in different tracks of the gradient PAGE separation. Thus in the chart or diagram of FIG. 2 tracks c–f represent the enzyme treated samples, track b represents the separation of the complete set of pHNO$_2$ fragments I, II and III (FIG. 1B) without enzyme treatment, and the original fragment alone (Fragment I) is shown in track a. This read-out then allows the majority of the sequence of Fragment I to be read. The manner of detection of the fragments will of course depend on the nature of the tag, but will most commonly be by fluorescence and fluorographic methods, or by a calorimetric method using for example a biotin/avidin detection technique as known in the art.

To summarise, in FIG. 2 the identity of the samples in the different tracks is as follows:

a) Fragment I
b) Partial HNO$_2$ hydrolysate of fragment I (pHNO)
c) pHNO$_2$+iduronate-2-sulphatase (I2Sase)—band shift marker* d) pHNO$_2$+glucuronidase (Gase)—band shift marker $ e) pHNO$_2$+iduronidase (Idase)—band shift marker ∞ f) pH$_2$+iduronate-2-sulphatase+iduronidase—band shift markers σ and τ

Running conditions for such gel electrophoresis may be as described previously in the literature, e.g. Turnbull and Gallagher (1988) *Biochem J*. 251, 597–608. The migration banding pattern depicted in FIG. 2 reflects tile different mobilities of saccharides with 2, 4, 6 and 8 sugar units (dp2–8).

Further Detailed Description Applicable to Example 1 of the Treatment of Fluorescent Tagged Saccharides With Exoenzymes and of Separation of the Treated Saccharides by Page As described above, in treating tagged saccharides generated by partial HNO$_2$ hydrolysis (pHNO$_2$) with exoenzymes, the mixed set of saccharides is divided into an appropriate number of aliquots (one for each set of exoenzyme digestion conditions and one left untreated). Thus, a pHNO$_2$ treated sample of final volume 125 μL may be divided into 5 aliquots of 25 μL, allowing sufficient for 4 different exoenzyme treatments. Each aliquot would contain approximately 200–400 pmoles of saccharide. Treatment with exoenzymes requires addition of 10 μL of exoenzyme buffer (200 mM sodium acetate buffer, pH 4.0), 2 μL of 2 mg/mL bovine serum albumin, 2 μL of appropriate enzyme (at concentrations of 3–6 U/ml where 1U=1 μmole substrate hydrolysed per minute) and distilled H$_2$O to bring the final volume to 40 μL. The samples are then incubated at 37° C. for 30–120 minutes which is usually sufficient to obtain complete digestion. The latter is important to the sequencing process since incomplete digestion would create a more complex banding pattern and would give a false indication of sequence heterogeneity. Where combinations of exoenzymes are required, these can be incubated sequentially or simultaneously with the sample. Where an enzyme with a different pH optima is used, an alternative buffer can be used both to terminate the pHNO$_2$ reaction and during setting up of the actual enzyme digestion. If necessary, the activity of one enzyme can be destroyed prior to a secondary digestion with a different enzyme by heating the sample at 100° C. for 1–5 minutes. Sample volumes can conveniently be reduced prior to electrophoresis by centrifugal evaporation.

The method of separating the treated saccharides for sequencing purposes by polyacryiamide gel electrophoresis (PAGE) is very effective and, as already mentioned in connection with purification gradient PAGE is particularly useful since it allows good resolution of a broad size range of saccharides on a single gel. The basic method, designated oligosaccharide mapping has been described in detail as previously indicates by Turnbull and Gallagher (again see *Biochemical Journal* (1988) 251, 597–608 and *Biochemical Journal* (1991) 265, 715–724). Briefly, gradient PAGE gels, typically 16–32 cm in length and 0.5–3 mm in thickness, comprising a long resolving gel (with gradients of total acrylamide concentrations in the range T20–50% and cross-linker ranging from C0.5% to C5%) and a short stacking gel (typically T5% acrylamide) are prepared using the buffer system described above. Samples (typically 10–20 μL in 10% glycerol) are loaded into wells in the stacking gel and run into the gel at 150 volts for 30 minutes, followed by electrophoresis at 200–1000 volts until the run is complete (i.e migration of marker dyes to predetermined positions). Visualisation of resolved fluorescent ABA-saccharide conjugates (picomole amounts) is readily achieved using a UV transilluminator (312 nm wavelength). They appear as sharp bright violet fluorescent bands easily visible to the naked eye. Improved sensitivity can be achieved using a charge coupled device (CCD) camera.

For sequencing purposes the gel should be loaded with a sample of intact tagged saccharide and of pHNO$_2$ generated saccharides not treated with exoenzymes, as well as the pHNO$_2$ samples actually treated with appropriate exoenzyme combinations. This allows the running position of the intact saccharide and pHNO$_2$ generated saccharides to be compared directly with the exoenzyme-treated saccharides (as shown in FIG. 2).

Interpretation of Migration Banding Pattern in FIG. 2

The migration banding pattern in FIG. 2 will next be described in more detail. Track (a) illustrates the size of the original fragment and track (b) shows the banding pattern after the initial pHNO$_2$ treatment. The presence of two additional bands at dp6 and dp4 identifies GlcNSO$_3$ residues at positions (2) and (4) in Fragment I (FIG. 1). No disaccharide band is seen so it can be deduced that the amino sugar at position (6) is GlcNAc. Since GlcNAc must be α1,4 linked to GlcA, it can also be deduced that this latter residue is present at position (7). After treatment with iduronate-2-sulphatase (track c) it is seen that only the original fragment shifts position (band *) thereby indicating a 2-O-sulphate group on unit (1). Since β-glucuronidase (track d) only shifts the position of the band ($) representing Fragment II (dp6), this identifies GlcA as being the residue at position (3). Iduronidase (track e) causes a shift only in the band (∞) representing Fragment III , so unsulphated iduronate is at position (5). Finally, the combination of iduronate-2-sulphatase and iduronidase (track f) causes a shift in mobility of both Fragment III (τ) and Fragment I (σ). In the latter case the shift in mobility exceeds that with the sulphatase enzyme alone (track c; band *). This confirms that the sugar residue at position (1) is iduronate-2-sulphate which becomes accessible to iduronidase after enzymic removal of the 2-O-sulphate group. The banding pattern in FIG. 2 thus enables the following features of the sequence of Fragment I to be read.

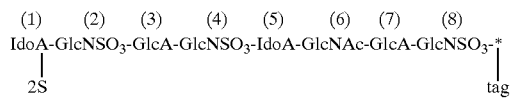

6-Sulphation at GlcNSO$_3$ or GlNAc

The presence of the 6-O-sulphate groups on the amino sugars at units (4) and (6) in Fragment I (FIG. 1) cannot be identified from the particular banding pattern illustrated in FIG. 2. However, 6-O-sulphation of amino sugars can be easily detected by introducing an extra track (not shown) in which a further portion of the mixture of the pHNO$_2$ fragments is treated with a combination of the iduronate-2-sulphatase, iduronidase and glucuronidase exoenzymes to ensure removal of the end chain hexuronates, together with glucosamine 6-O-sulphatase which will remove the 6-O-sulphate groups from the amino sugars now exposed at the ends of the fragments. The loss of 6-O-sulphate would be picked up by a mobility shift on gradient PAGE. Consider, for example, the 6-O-sulphate at unit 4 (FIG. 1). This would be present in Fragment II (dp6) after pHNO$_2$ (track b in FIG. 2). Enzymic removal of the terminal GlcA in this Fragment II produces a dp5 fragment (track d; symbol $). This structure has an exposed GlcNSO₃(6S) (unit 4) at the non-reducing end (NRE) and the 6-O-sulphatase enzyme would then remove the 6-O-sulphate causing a further increase in mobility.

Additional Approaches for Sequencing Contiguous N-acetylated Sequences

When sequencing HS/heparin saccharides there will sometimes be cases where one or more N-acetylated disaccharides intervene within an otherwise N-sulphated disaccharide sequence. This means that the pHNO₂ treatment cannot create a new reducing end for exoenzyme attack and this would limit the sequence information which can be obtained at some positions. For example, Fragment I in the present example contains a GlcNAc residue at position 6, and therefore pHNO₂ does not create a fragment corresponding to positions 7 and 8. This means that these residues will not be directly sequenced. However, this problem can be overcome using the exoenzyme N-acetylglucosaminidase. Fragment III produced by pHNO₂ can be treated with iduronidase (to remove the iduronic acid residue at position 5), glucosamine-6-sulphatase (to remove tie 6-O-sulphate on the GlcNAc at position 6) and then N-acetylglucosaminidase (to remove the GlcNAc residue at position 6). This would result in a fragment corresponding to positions 7 and 8 (i.e. GlcA-GlcNSO₃*) and would allow the sequencing of the residues at these positions as already described as if the terminal uronate residue at position 7 had been created by the pHNO₂ treatment. If more than one GlcNAc residue intervenes, this process can be reiterated any number of times. Based on what is currently known about the structure of heparan sulphate, in such a case the sequence is likely to consist of repeating GlcA-GlcNAc residues predominantly without O-sulphate substitutents. It would thus be necessary to deactivate the glucuronidase or N-acetylglucosaminidase after each individual digestion to allow each shift to be individually identified (i.e. to prevent a contiguous sequence of such residues being degraded in a single step as would occur with a combination of both enzymes).

Sequence Microheterogenicity

It is also possible that two closely-related structures will run as a single band on gradient PAGE. The sequencing strategy described would however detect this type of variability in sequence. Imagine for example that in position (3) some chains contained IdoA rather than GlcA—there would then be both hexa and penta bands after the glucuronidase (track d) and iduronidase (track e) treatments in proportion to the frequency of occurrence at position (3). A track in which both enzymes Gase and Idase are used would effect a complete shift in the bands from hexa to penta and this would be clearly apparent.

There could also be variation in the sequence of N-sulphated (GlcNSO₃) and N-acetylated (GlcNAc) glucosamine residues. This could be detected, however, by use of N-acetylglucosaminidase which acts only on non-reducing end (NRE) unsubstituted GlcNAc units. If for example, the GlcNSO₃ unit at position (2) was occasionally GlcNAc this could be detected by running an extra track of the pHNO₂ saccharide mixture incubated with an iduronidase, I2Sase, and Gase cocktail, heat inactivating the enzymes then incubating with N-acetylglucosaminidase. If unit (2) is always GlcNSO₃ there will be no reduction in molecular size beyond dp7. The presence, however, of GlcNAc in a proportion of the saccharides would then be revealed by an extra band at dp6 (hexa).

Further Options for Sequencing

HS and heparin may also contain O-sulphate groups at C-3 of GlcNSO₃— and and at C-2 of GlcA units. However exosulphatase enzymes are known that can specifically remove these substituents (see for example Irwin G. Leder (1980), "A novel 3-O sulfatase from human urine acting on methyl-2-deoxy-2-sulfamino-α-D-glucopyranoside 3-sulphate", *Biochemical and Biophysical Research Communications*, 94, 1183–1189; Ulf Lindahl et al, (1980), "Evidence for a 3-O-sulfated D-glucosamine residue in the antithrombin-binding sequence of heparin", *Biochemistry*, 77, 6551–6555; Craig Freeman and John J Hopwood (1989) "Human liver glucuronate 2-sulphatase". *Biochem. J.*, 259, 209–216 and Craig Freeman and John J Hopwood (1992) "Human α-L-iduronidase", *Biochem. J.*, 282, 899–908). These enzymes may therefore also be incorporated into the sequencing strategy. Likewise, (exo)N-sulphamidase (see for example Craig Freeman and John J Hopwood (1986) "Human Liver Sulphamate sulphohydrolase", *Biochem. J.*, 234, 83–92) could be used to confirm the presence of N-sulphate groups.

As previously indicated a number of alternatives to pHNO₂ are also available for the initial partial depolymerisation and specific cleavage of internal linkages. Examples of known alternative reagents or treatments include hydrazinolysis followed by treatment at pH 4.0 with HNO₂ (cleaves GlcNAc→HexA linkages), and also use of the endoenzymes heparitinase (cleaves GlcN.R→GlcA linkages) and heparinase (cleaves GlcNSO₃(±6S)→IdoA(2S) linkages). These latter lyase enzymes can also provide valuable sequence information on the nature of the hexuronate residues. Further sequencing of heparinase/heparitinase fragments may require removal of the NRE unsaturated HexA(±2S) residue generated by the endolytic mode of these enzymes which involves an eliminative cleavage mechanism, but this can be easily achieved by treatment with specific bacterial enzymes (glycuronate sulphatase and glycuronidase) or mercuric salts (see for example U. Ludwigs et al (1987) "Reaction of unsaturate uronic acid residues with mercuric salts" *Biochem. J.*, 245. 795–804).

In principle the method of the present invention is applicable to saccharide fragments of any size and in practice its effective range will be limited only by the resolving power of separation techniques currently available.

Moreover, as already mentioned, the principle of this sequencing method is also applicable to sequence analysis of saccharides excised from other glycosaminoglycans (GAG's), glycoproteins or other saccharide chain containing material. Since an N-acetylated amino sugar is present as a component of all disaccharide units in GAG's, saccharides of interest can be cleaved at the GlcNAc/GalNAc hexosaminidic linkage by partial hydrazinolysis/pH 4.0 HNO₂ to yield fragments that can then be sequenced by use of appropriate exoglycosidases and exosulphatases following the procedures herein described. Alternatively partial scission can be achieved by GAG-specific enzymes (e.g. chondroitinase AC and ABC for chondroitin and dermatan sulphate and keratanase for keratan sulphate). End-chain tagging and separation techniques would be similar to those described for HS/heparin.

EXAMPLE 2

Figure 3:
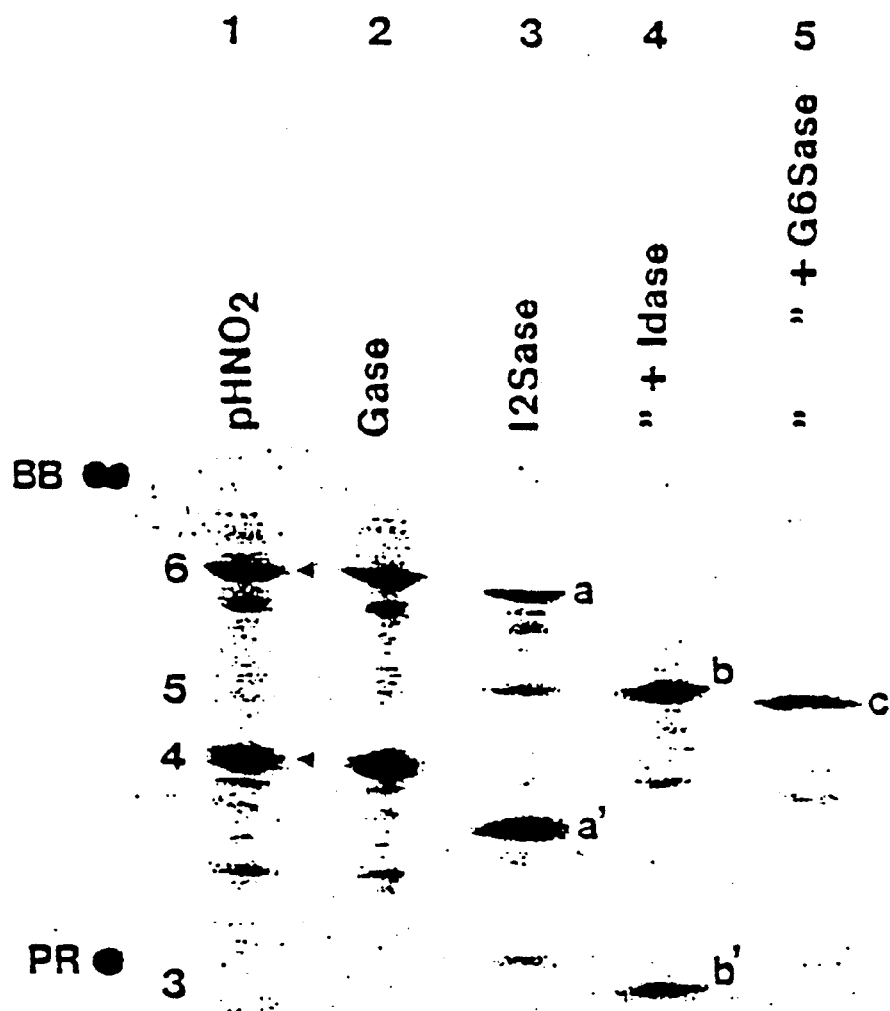
FIG. 3 is a photocopy of a photographic representation of a electrophoretic gel banding pattern derived from some preliminary studies undertaken during development of the present invention.

By way of a further explanatory example there is shown in FIG. 3 a polyacryiamide gel electrophoresis banding pattern derived from some preliminary studies, depicting some aspects of the exosequencing method of the present invention applied to a $^{35}S$ metabolically-labelled hexasaccharide fragment having the following simple repeating structure:

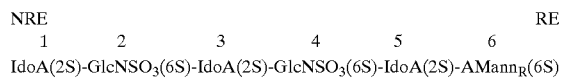

A test sample of this fragment was first treated with $HNO_2$ under conditions designed to produce only hydrolysis and partial depolymerisation of susceptible linkages. The resulting mixture of $pHNO_2$ fragments (dp 6, 4 and 2) was then desalted by gel filtration and resolved on a 32.5–40% gradient PAGE gel, either intact (i.e. without further treatment) or after treatment with different combinations of exoenzymes. Combination treatments were carried out sequentially in the order shown.

The tracks indicated in FIG. 3 were as follows (BB and PR indicate the running positions of bromophenol blue and phenol red marker dyes)

(1) Untreated $pHNO_2$ fragments
(2) Gase only
(3) I2Sase only
(4) I2Sase+Idase
(5) I2Sase+Idase+G6Sase The $pHNO_2$ treatment (track 1) resulted in the expected major bands at the dp6 and dp4 positions (arrowed) and it is the shifts in these bands that need to be observed for sequencing purposes. The dp6 arrowed band corresponds to the intact original fragment. The dp4 arrowed band represents the structure

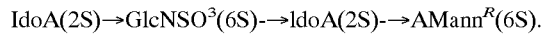

(n.b. in this particular example the dp2 products migrated off the gel and are not therefore seen).

With regard to the exoenzyme treatments, the results show a clear stepwise removal of NRE residues. Gase has no effect (track 2). I2Sase acts to remove a 2-O-sulphate group from both the dp6 and dp4 bands resulting in shifts (track 3, bands a and a' respectively). Idase then acts to remove an iduronic acid residue, resulting in penta- and tri-saccharide products (track 4, bands b and b' respectively). G6Sase can then act to remove a 6-O-sulphate group giving a further shift (track 5, band c). (NB: the removal of the 6-O-sulphate from the trisaccharide b' resulted in its loss from the pattern due either to migration off the gel or possibly lack of retention on a nylon membrane to which the separated fragments were transferred from the gel for fluorographic detection of the radiolabelled material.

Although in this test example the saccharide material was not selectively labelled and end referenced, the foregoing practical results confirm that $pHNO_2$ can be used for partial depolymerisation and that exoglycosidases and exosulphatases act on NRE sugar residues to produce the predicted shifts in mobilities of oligosaccharide fragments.

Thus, these results, although only performed on a small test sample, clearly demonstrate not only that the exosequencing strategy can be used to determine rapidly and unequivocally the sequence of monosaccharide residues and sulphate groups at the NRE terminus of HS/Heparin fragments, but in addition they show that this general strategy can be applied to newly created NRE terminii generated by partial internal cleavage of a fragment at $GlcNSO_3$ residues with a selective scission reagent such as $HNO_2$.

Alternative Sequencing Strategy Involving Selective Coupling of Saccharides to a Solid Phase Support An alternative to tagging the chains of the saccharide material with a detectable labelling compound specifically at the reducing end for sequencing purposes is to couple or attach them to a solid-phase support selectively via their reducing ends. The partial internal cleavage (e.g. $pHNO_2$) of glycosidic linkages can then be carried out whilst the saccharide chains are thus immobilized and fragments which are no longer contiguous with the reducing end can be easily removed by thorough washing. Provided a method is available then to release the saccharides attached at their reducing ends from the solid phase support, a mixed set of saccharide chain fragments equivalent to those created by $pHNO_2$ treatment of fluorescent tagged saccharides is obtained. In effect, this again provides a reducing end referencing feature. Such an approach has been described previously to obtain "end-referenced" polysaccharide chains by Radoff and Danishefsky (1984), *J. Biol. Chem.*, 259, 166–172 who attached a coupling agent (tyramine) to the reducing end terminus of heparin saccharide chains for coupling to an insoluble activated Sepharose™ matrix.

In this method the saccharide chains of the saccharide material will usually be selectively modified by first attaching as a tag to their reducing ends a coupling agent for the coupling to the solid phase support. However, in the case of sequencing the saccharide component of material such as proteoglycans for example where the reducing ends of the saccharide chains are already joined or conjugated to polypeptide chains, no initial modification may be needed as these existing polypeptide chains may be used directly to couple to on appropriate solid phase matrix support, e.g. CNBr-activated Sepharose 4B™, as described for example by Lyon et al (1987) *Biochem. J.* 242, 493–498 and by Turnbull and Gallagher (1991) *Biochem. J.* 277, 297–303).

This approach involving immobilizing the saccharide material by coupling to a solid phase support can be particularly suited to carrying out the sequence analysis method of the present invention on small amounts of sample (for example, as from cultured cells) radiolabelled biosynthetically (for example with 3H-glucosamine).

In practice, the procedure may also be modified slightly in that the partial depolymerisation step may be carried out before coupling and immobilizing the saccharide chains or fragment thereof on the solid phase support. For example, the saccharides can first be tagged specifically at the reducing ends with a coupling agent in the form of 2-imino-biotin hydrazide, and then they can be subjected to $pHNO_2$ treatment as already described. After the $pHNO_2$ treatment the fragments can then be captured on avidin-agarose by virtue of the reducing end biotin residues. Following thorough washing, the saccharides remaining attached can be dissociated from the gel under mild conditions by eluting the gel with a pH 4 buffer. The recovered saccharides can then be sequenced directly, again as already described. After electrophoresis they can be conveniently detected by electrotransfer to nylon membrane material and fluorography, again as described in the literature (see again Turnbull and Gallagher in *Biochemical Journal* (1988) 251, 597–608 and in *Biochemical Journal* (1991) 265. 715–724).

As will be seen, the invention provides a number of different aspects and. in general it embraces all novel and inventive features and aspects herein disclosed either explicitly or implicitly and either singly or in combination with one another. Moreover, the scope of the invention is not to be construed as being limited by the. illustrative examples or by the terms and expressions used herein merely in a descriptive or explanatory sense, and many modifications may be made within the scope of the invention defined in the appended claims.

What is claimed is:

1. A method of analyzing and sequencing saccharide material composed of saccharide chains having more than three monosaccharide units interconnected through glycosidic linkages that are not all identical, wherein each saccharide has a referencing feature at its reducing end, said method comprising the sequential steps of:
   (a) treating said saccharide material in a partial depolymerisation stage with a selective scission reagent that acts in accordance with a predetermined linkage specificity as an endoglycosidase to substantially cleave internal glycosidic linkages spaced from the non-reducing end of the saccharide chains, thereby producing a mixed set of saccharide chains comprising intact chains and fragments of intact chains having different lengths representative of the full spectrum of all possible lengths given the particular glycosidic linkage specificity of the selective scission reagent employed,
   (b) treating a sample or samples of said mixed set of saccharide chains and chain fragments from the partial depolymerization treatment of step (a) with a set of exoenzymes which includes exoglycosidases of known specificity that cleave only particular glycosidic linkages at the non-reducing end of saccharide chains, said exoenzymes being applied, either singly or in combination, in accordance with a predetermined strategy,
   (c) continuing step (b) to an extent sufficient to obtain complete digestion and cleave susceptible linkages at the non-reducing end of all the saccharide chains, and then,
   (d) analyzing said sample or samples to detect the saccharide chain fragments generated by cleavage treatments, said fragments having a reducing end derived from the reducing end of the corresponding chain in the original saccharide material, and at least partially deducing the monosaccharide sequence in the saccharide material.

2. A method as claimed in claim 1, wherein said saccharide chains have attached to their reducing ends a detectable label or tag providing a reducing end reference feature, wherein said label or tag is selected from the group consisting of a radiochemical labeling agent, a fluorescent labeling agent and a calorimetrically detectable labeling agent.

3. A method as claimed in claim 2 wherein the detectable label or tag of the reducing end referencing feature comprises a compound selected from the group consisting of anthranilic acid, an aminocoumarin hydrazide and a tritiated borohydride.

4. A method as claimed in claim 1 further comprising, before step (a), a step of modifying said saccharide chains by attaching to their reducing ends a tag comprising a coupling agent for immobilizing said chains or reducing end fragments thereof by coupling to a solid phase support, while fragments of said chains produced by the partial depolymerization treatment which are not contiguous with the reducing ends of original undegraded chains are separated and removed.

5. A method as claimed in claim 4 including the step of coupling the saccharide chains to a said solid phase support to immobilize said chains, followed by a step of separating and removing fragments of said chains produced by the partial depolymerization treatment which are not contiguous with the reducing ends of the original undegraded chains, followed by the step of releasing residual immobilized saccharide chain fragments from said solid phase support prior to the exoenzyme treatment of step (b).

6. A method as claimed claim 1 wherein the selected exoenzymes further include specific exosulphatases for selective removal of sulphate groups from monosaccharide residues at the non-reducing end of said saccharide chains or fragments of said chains.

7. A method as claimed in claim 1 wherein the selective scission reagent used in step (a) for the controlled partial depolymerization of the saccharide material is a member selected from the group consisting of nitrous acid and endoglycosidase enzymes.

8. A method as claimed in claim 7 wherein said selective scission reagent is nitrous acid introduced to said saccharide material under low pH conditions whereby said acid specifically cleaves hexosaminidic linkages that link an N-sulphated amino sugar to a hexuronate residue but not hexosaminidic linkages that link an N-acetylated amino sugar to a hexuronate residue.

9. A method as claimed in claim 1 wherein the partial depolymerization treatment of step (a) is carried out by treating separate samples of the saccharide material with said selective scisson reagent for different periods of time and then pooling the products to provide the mixed set of chain fragments for use in step (b), thereby ensuring that the lengths of the saccharide chain fragments in said mixed set of chain fragments used in step (b) are distributed throughout the range extending from full length undegraded chains to minimum length chain fragments lacking in further internal glycosidic linkages cleavable by said selective scission reagent.

10. A method as claimed in claim 1 in which one sample of the mixed set of saccharide chain fragments produced by the partial depolymerization of the saccharide material in step (a) is subjected without exoenzyme treatment to a separation procedure to separate said chain fragments according to length, and other samples are also subjected, separately, to the same said separation procedure to separate the saccharide chain fragments therein according to length and composition after each of these other samples has been treated with a different exoenzyme or combination of exoenzymes in step (b).

11. A method as claimed in claim 1 wherein the analysis of step (c) includes separating the saccharide chain fragments produced by the cleavage treatments according to their length and composition.

12. A method as claimed in claim 11 wherein the separated saccharide chain fragments that include the reducing end residues of the original saccharide chains of the saccharide material are detected by detecting a label or tag carried by the separated saccharide chain fragments.

13. A method as claimed in claim 11 wherein said separation of the saccharide chain fragments is effected by an electrophoretic separation technique whereby the saccharide fragments are separated according to differences in length and composition which result in different mobilities in the electrophoretic medium.

14. A method as claimed in claim 13 which comprises treating separate samples of the mixed set of saccharide chain fragments from step (a) with different said exoenzymes, either singly or in combination, carrying out step (b) and subjecting said samples simultaneously in step (c) to electrophoretic separation in different tracks of an electrophoresis gel, thereby providing a migration banding pattern representative of the different gel mobilities of the separated fragments having differences in length and/or composition.

15. A method as claimed in claim 14 wherein the electrophoretic separation is carried out by gradient polyacryiamide gel electrophoresis (gradient PAGE).

16. A method as claimed in claim 14 which includes transferring the separated saccharide chain fragments by an electrotransfer technique to a synthetic polyamide membrane after termination of the electrophoresis.

17. A method as claimed in claim 1 wherein labeled or "tagged" fragments that include the reducing and residues of the original saccharide chains of the saccharide material provide in the analysis of step (c) a visually-detectable pattern which, in conjunction with the known specificity of the exoenzymes used in step (b), gives sequence information directly by deduction.

18. A method as claimed in claim 1 in which the saccharide material is composed of saccharide chains containing amino sugar residues and sulphated monosaccharide units, and the exoenzymes used in step (b) are selected from the group consisting of a glucuronidase, an iduronidase, an N-acetylglucosaminidase, an iduronate-2-sulphatase, a glucuronate-2-sulphatase, a glucosamine-6-sulphatase, a glucoasmine-3-sulphatase and a sulphamate sulphohydrolase.

* * * * *